United States Patent [19]

Kawada et al.

[11] 4,123,554

[45] Oct. 31, 1978

[54] FUNGICIDAL AND GERMICIDAL BENZANILIDES

[75] Inventors: Seigo Kawada, Fujieda; Yoshitaka Suda, Shizuoka; Shigeru Tsuchiya, Shimizu; Nobuya Ohta; Norimichi Muramatsu, both of Shizuoka; Kazuo Nishio, Shimizu, all of Japan

[73] Assignee: Kumiai Chemical Industry Co., Ltd., Tokyo, Japan

[21] Appl. No.: 740,878

[22] Filed: Nov. 11, 1976

Related U.S. Application Data

[63] Continuation-in-part of Ser. No. 585,078, Jun. 9, 1975, abandoned.

[30] Foreign Application Priority Data

Jun. 12, 1974 [JP] Japan ................................ 49/66767
Jan. 21, 1975 [JP] Japan ................................ 50/8981

[51] Int. Cl.² ............... C07C 103/78; A61K 31/165
[52] U.S. Cl. ........................... 424/324; 260/558 D; 260/558 P
[58] Field of Search ................. 260/558 P, 558 D; 424/324

[56] References Cited

U.S. PATENT DOCUMENTS

| 3,340,042 | 9/1967 | Schwartz et al. | 71/94 |
| 3,721,709 | 3/1973 | Mueller et al. | 260/558 P X |
| 3,839,446 | 10/1974 | Teach | 260/557 R X |
| 3,885,948 | 5/1975 | Baker et al. | 260/553 A X |
| 3,903,155 | 9/1975 | Teach | 260/558 P X |
| 3,937,840 | 2/1976 | Chiyomaru et al. | 424/324 |
| 3,969,510 | 7/1976 | Osieka et al. | 424/324 |
| 3,981,814 | 9/1976 | Nikawitz | 260/558 P X |
| 3,985,804 | 10/1976 | Chiyomaru et al. | 260/558 P |
| 4,069,335 | 1/1978 | Kawada et al. | 424/324 X |

FOREIGN PATENT DOCUMENTS 1,217,868 12/1970 United Kingdom.

OTHER PUBLICATIONS

"Correlation between Chemical Structure and Rodent Repellency of Benzoic Acid Derivatives", Fearn et al., J. Agr. Food Chem., 13, 1965, pp. 116–117.
White et al., CA 83:173722d (1975).

Primary Examiner—Thomas A. Waltz
Attorney, Agent, or Firm—Stevens, Davis, Miller & Mosher

[57] ABSTRACT

The present invention relates to a compound having the following general formula (I):

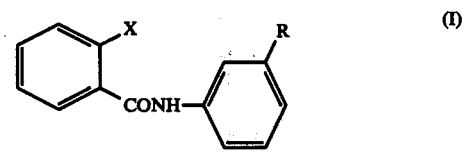

wherein X stands for a halogen atom or a methyl radical; and R stands for an alkyl or alkoxy radical containing 3 to 6 carbon atoms provided that R represents an alkyl radical containing 3 to 6 carbon atoms when X is a methyl radical, a process for the production thereof, an agricultural composition containing the said compound as an effective component, and a method for preventing and healing the diseases of the plant and in soil using the said compound.

16 Claims, No Drawings

FUNGICIDAL AND GERMICIDAL BENZANILIDES

CROSS REFERENCES TO RELATED APPLICATION:

The present application is a continuation in part application of U.S. patent application Ser. No. 585,078 filed on June 9, 1975, now abandoned.

BACKGROUND OF THE INVENTION

The present invention relates to a compound having the formula (I)

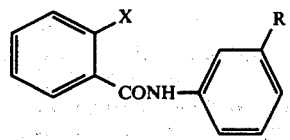

wherein X stands for a halogen atom, a methyl radical and R stands for alkyl or alkoxy radical containing 3 to 6 carbon atoms, provided that R is an alkyl radical containing 3 to 6 carbon atoms when X is a methyl radical, and the process for producing the compound having the formula (I).

The present compound above has a germicidal effect and is suited for germicidal use in agricultural and horticultural use. Therefore the present invention is also directed to a germicide for agricultural and horticultural use and a method for preventing and healing diseases in plants and in soil.

The agricultural and horticultural germicide of the present invention containing as the active ingredient the compound having the formula (I) are effective to protect plants from the diseases such as rice sheath blight and bacterial leaf blight; tomato leaf blight; cucumber anthraenose; haricot stem rot; alternnaria leaf spot and powdery rot; wheat bund; rust of wheat; barley turf or coffee; cereals grasses smat and rhizoctonia and fusarium soil disease; and also are effective as a disinfectant for seed.

DESCRIPTION OF THE PRIOR ART

The plant protecting effect and germicidal effect of benzanilide derivatives have already been described in German OLS No. 1,907,436 and British Pat. No. 1,217,868. The above-mentioned German OLS relates to o-methylbenzanilide whereas the above-mentioned British patent relates to a germicide containing as the active ingredient a benzanilide derivative represented by the following general formula:

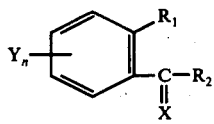

The compound in the present invention corresponds to the above general formula where $R^1$ is a halogen atom, a methyl, nitro or acetyloxy radical, $Y_n$ is a hydrogen atom, X is an oxygen atom and $R^2$ is $-NR^3R^4$ wherein $R^3$ is a hydrogen atom and $R^4$ is m-alkylated or m-alkoxylated phenyl radical. The compounds of the present invention, however, are not specifically described in the above-mentioned patents, and provide stronger germicidal effect and longer duration of effect and are harmless to the useful plants as described in the following, in comparison with the compounds disclosed in the German OLS No. 1,907,436 and British Pat. No. 1,217,868.

SUMMARY OF THE INVENTION

The object of the present invention is to provide a compound having the formula mentioned above.

Another object of the present invention is to provide a method for preventing and healing the diseases of the plant and in the soil.

Still another objects of the present invention will become apparent from the descriptions and examples of the present invention.

DESCRIPTION OF THE PREFERRED EMBODIMENTS

As explained above, the present invention refers to a benzanilide compound having the formula (I), and for preventing and healing the diseases of plants.

As explained in the foregoing, the compounds of the present invention are provided with an excellent preventive and therapeutic effect against the sheath blight of rice plant and the rust of fruits, vegetables, crops, flowers, coffee etc. and are capable of preventing the diseases by various treatments such as spraying, coating, submerged application, soil treatment, powder coating on seeds etc. Further said compounds are provided with additional advantageous properties of penetrating into the plant organism to retain the effect thereof for a long period and of very low toxicity for warm-blooded animals, presenting no abnormality on oral administrations of 10,000 mg/kg to mice.

The excellent preventive and therapeutic effect of the present compounds over the known compounds will be clear from the test results as shown hereinafter.

The active ingredient of the present invention can be used in a form of the conventional preparations, e.g. solution, emulsion, wettable powder, fine granules, granules and dust, but it is also possible to use the ingredient by itself.

The compounds of the present invention can be prepared according to any of the following reactions:

Reaction (A)

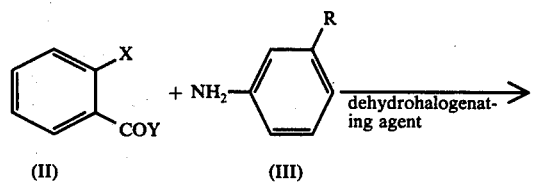

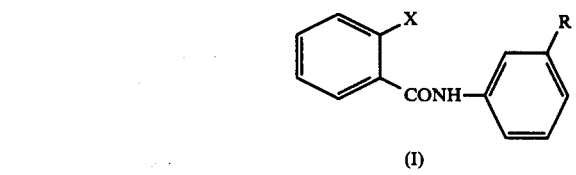

Reaction (B)

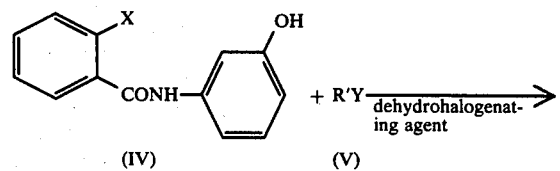

-continued

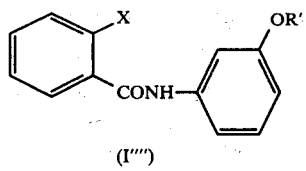

Reaction (C)

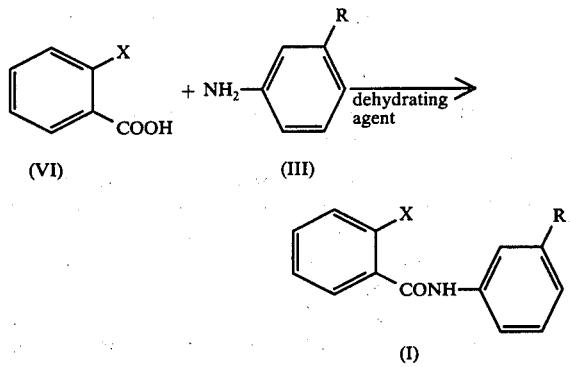

The above reactions can be carried out with a molar ratio of the reactants of about 0.95 to 1.20 and under ordinary reaction conditions as shown in the following examples to obtain the desired compounds.

As a dehydrohalogenating agent in the reaction (A) there is used preferably tertiary amines such as triethylamine, dimethylaniline or pyridine, carbonates such as sodium carbonate or sodium bicarbonate or the same object may be obtained by using two or more molar amount of aniline derivative reactants.

The reaction medium may be a solvent inert to benzoyl halide or aniline derivatives such as benzene, toluene, acetone, ether, dioxane or acetonitrile.

The reaction may be carried out at a temperature within a range from −20° C. to 100° C.

As the dehydrohalogenating agent in the reaction (B) there may be used alkali hydroxide such as sodium hydroxide or potassium hydroxide, besides the aforementioned tertiary amines and carbonates.

As the dehydrating agent in the reaction (C) there may be used phosphorous compounds such as phosphorous trichloride, phosphorus oxychloride, phosphorous pentachloride, phosphorous tribromide or phosphorous pentoxide, thionyl chloride, sulfuryl chloride, sulfonic acids, sulfuric acid, hydrohalogenic acids, carbodiimides, oxides such as alumina or silica gel.

The reaction medium may be water or alcohols besides the solvent usable for the reaction (A), and the reaction can be carried out in a good yield at a reaction temperature within a range −20° C. to 100° C.

Typical preparations of the compounds of the invention will be described in the following examples.

EXAMPLE 1

Preparation of 3'-isopropoxy-2-bromobenzanilide 21.0 g (0.1 mole) of o-bromobenzoyl chloride was added dropwise, under agitation and cooling, to a mixture of 15.1 g (0.1 mole) of m-isopropoxyaniline and 8.4 g (0.1 mole) of sodium bicarbonate in 200 ml of acetone.

After the addition, the reaction mixture was heated to 40° to 50° C. and kept at this temperature for 5 hours.

Successively the reaction mixture was poured into 500 ml of iced water, and the formed oily material was extracted with benzene. The benzene layer was washed with water and then dried over anhydrous sodium sulfate. The product obtained after removal of benzene was crystallized from a mixture of benzene and n-hexane (1:3 ) to obtain 26.4 g (79.1% yield) of colorless prism crystals having a melting point of 89°–91° C.

EXAMPLE 2

Preparation of 3'-isopropoxy-2-iodobenzanilide 1.5 of potassium hydroxide and then 7.5 g of 3'-hydroxy-2-iodobenzanilide were dissolved in ethanol. To the obtained solution was further added 3.2 g of isopropylbromide and the obtained mixture was heated to 50° to 70° C. for 5 hours.

After cooling, the reaction mixture is poured into 200 ml of water alkalinified with sodium hydroxide, and the resulting crystals were separated by filtration, washed with water and recrystallized from a benzene-n-hexane mixture to obtain 7.1 g (62.3%) of colorless prism crystal having a melting point of 94°–96° C.

EXAMPLE 3

Preparation of 3'-isopropyl-2-methylbenzanilide 13.6 g (0.1 mole) of o-toluic acid and 13.6 g (0.1 mole) of m-isopropylaniline were dissolved in 100 ml of chlorobenzene, and 11.9 g (0.1 mole) of thionyl chloride was added dropwise to the resulting solution at a reaction temperature of 40° to to 50° C. After the addition, the mixture was maintained at 90°–95° C. under agitation for 4 hours during which sulfur dioxide and hydrogen chloride gas were continuously generated.

After the reaction, chlorobenzene was distilled off from the reaction mixture, and the residue was recrystallized from n-hexane to obtain 24.1 g of colorless needle crystals having a melting point of 70°–71° C.

The typical active ingredients prepared by the processes of the present invention are as follows, which will hereinafter be referred to by the compound numbers also indicated in the following.

Compound No. 1
   3'-n-propoxy-2-chlorobenzanilide
   Pale yellow oil     b.p. 172–175° C/ 0.02 mmHg Compound No. 2
   3'-isopropoxy-2-chlorobenzanilide
   Pale yellow oil     b.p. 173–175° C/ 0.007 mmHg Compound No. 3
   3'-isopropoxy-2-bromobenzanilide
   Colorless prism     m.p. 89–91° C Compound No. 4
   3-isopropyl-2-bromobenzanilide     m.p. 79–80° C Compound No. 5
   3'-isopropyl-2-iodobenzanilide     m.p. 112–113° C Compound No. 6
   3'-n-propoxy-2-iodobenzanilide
   Colorless needle     m.p. 114–115° C Compound No. 7
   3'-isopropoxy-2-iodobenzanilide
   Colorless prism     m.p. 94–96° C Compound No. 8
   3'-n-butoxy-2-iodobenzanilide
   Colorless needle     m.p. 102–105° C Compound No. 9
   3'-isobutoxy-2-iodobenzanilide
   Colorless needle     m.p. 139.5–141.5° C Compound No. 10
   3'-sec-butoxy-2-iodobenzanilide
   Colorless needle     m.p. 86–87° C Compound No. 11
   3'-n-pentyloxy-2-iodobenzanilide
   Colorless crystal     m.p. 115–118° C Compound No. 12
   3'-n-hexyloxy-2-iodobenzanilide -continued

| | |
|---|---|
| Colorless crystal | m.p. 112.5–113.5° C |
| Compound No. 13 | |
| 3'-isopropyl-2-methylbenzanilide | |
| Colorless needle | m.p. 70–71° C |
| Compound No. 14 | |
| 3'-tert-butyl-2-methylbenzanilide | |
| Yellow oil | b.p. 181–186° C |
| | 0.04–0.06 mmHg |
| Compound No. 15 | |
| 3'-tert-pentyl-2-methylbenzanilide | |
| Colorless crystal | m.p. 68–71° C |

The active ingredient of the present invention can be used in the form of conventional preparations, e.g. solution, emulsion, wettable powder, fine granules, granules or dust, but it is also possible to use the active ingredient by itself.

Such preparations can be obtained by mixing, in a conventional manner, the active ingredient with a diluting agent such a liquid or solid carrier and eventually with an emulsifier or a dispersing agent.

The liquid diluent or carrier can be water, aromatic hydrocarbons such as xylene, benzene or methyl naphtalene, chlorinated aromatic hydrocarbons such as chlorobenzene, mineral oil fractions such as paraffin, alcohols such as methanol or propanol, or polar solvents such as dimethylformamide or dimethylsulfoxide.

The solid diluent or carrier can be talc, clay, kaolin, hydrated silica, wood powder, sand etc. The emulsifier can be polyoxyethylene ester of aliphatic carboxylic acids, polyoxyethylene ether of aliphatic alcohols etc.

The dispersing agent can be alkali metal salts, alkaline earth metal salts or ammonium salts of alkyl sulfonic acids, alkylarylsulfonic acids or lignin sulfonic acids; methyl-cellulose etc.

The active ingredient can be combined with other germicidal compounds such as ferric ammonium salts of methane arsonic acid, Polyoxin (antibiotic fungicide), Validamycin (antibiotic fungicide) or phenazin-5-oxide, insecticidal compounds such as o,o-dimethyl-o-(3-methyl-4-nitrophenyl)-phosphorothioate, o,o-dimethyl-o-(3-methyl-4-methylthiophenyl)-phosphorothioate or hydrochloric acid salt of N-(2-methyl-4-chlorophenyl)-N,N-dimethylformamidine to impart synergistic effect.

It is also possible to combine with a fertilizer, soil conditioner, etc.

The compounds of the invention is preferably applied in the following quantities.

Solution
50–300 liters of 10–2,000 ppm solution per 10 a.
Powder
1–5 kg of 0.5–10% powder preparation per 10 a.
Soil treatment
100–5,000 g of the active ingredient per 10 a.
Seed treatment
Seeds are coated with 0.01–5 wt.% amount of the active ingredient.

Certain examples of formulations containing the active ingredients of the invention are given in the following for further clarification, though they are nlot intended to be limiting the invention.

Composition No. 1: Powder

A dust preparation is obtained by crushing and uniformly mixing 4% of the compound No. 1, 5% of diatomaceous earth and 91% of clay.

Composition No. 2: Wettable powder

A wettable powder preparation is obtained by uniformly mixing and crushing 50% of the compound No. 2 45% of diatomaceous earth, 2% of sodium dinaphthylmethane and 3% of sodium lignine.

Composition No. 3: Emulsion

An emulsifiable concentrate was obtained by uniformly mixing 30% of the compound No. 3, 20% of cyclohexanone, 11% of polyoxyethylene alkylaryl ether, 4% of calcium alkylbenzene sulfonate and 35% of methyl naphthalene.

Composition No. 4: Fine granules

Sea sand of 60–250 mesh (Tyler standard) was mixed and stirred thoroughly with 4% amount of polyethylene glycol to form uniform coating of polyethylene glycol on the sand. A fine granule preparation was obtained by thoroughly stirring 94% of the thus obtained mixture, and 6% of a mixture consisting of 70% of the compound No. 5 and 30% of clay.

Composition No. 5: Granules

10% of the compound No. 5, 2% of sodium lauryl sulfate, 5% of sodium lignine sulfonate, 2% of carboxymethyl cellulose and 81% of clay were uniformly mixed and crushed. The obtained mixture was added with 20% amount of water, kneaded, then extruded from an extrusion type granulating machine. The obtained granules were dried and sieved with a 14–32 mesh sieve (Tyler standard).

The agricultural effects of compounds of the invention are shown in the following experiments.

Test Example

Preventive effect on rice sheath blight

Porcelain pots of a diameter of 9 cm were filled with soil of rice paddy field, and water was added to simulate the condition in the rice field. nine stalks, in groups of three stalks each, of rice plant seedlings (*Oryza sativa L. var Kinmaze*) were planted and cultivated in each pot. When said seedlings reached the booting stage, the wettable powder preparations prepared according to the foregoing composition No. 2 were diluted with water to a given concentration and sprayed in an amount of 15 ml per pot. The rice sheath blight (*Pellicuralia Sasakii*) cultivated on potato sucrose agar medium was inoculated on the leaf sheath. The rice plants after the inoculation were placed in high humidity chamber (25°–30° C.), and the length of lesions formed in the leaf sheath path was measured after 10 days. The following table shows the results of three pots for each test.

$$\text{Protection value (\%)} = 1 - \frac{\text{Total length of lesions in treated plants}}{\text{Total length of lesions in non-treated plants}} \times 100$$

Table 1

| Compound | Concentration (ppm) | Total length of lesions (cm) | Protection value (%) | Phytotoxicity |
|---|---|---|---|---|
| Compound | | | | |
| No. 1 | 100 | 17.5 | 96.2 | None |
| No. 2 | " | 0 | 100 | " |
| No. 3 | " | 0 | 100 | " |
| No. 4 | " | 0 | 100 | " |
| No. 5 | " | 0 | 100 | " |
| No. 6 | " | 0 | 100 | " |
| No. 7 | " | 0 | 100 | " |

Table 1-continued

| Compound | Concentration (ppm) | Total length of lesions (cm) | Protection value (%) | Phytotoxicity |
|---|---|---|---|---|
| No. 8 | " | 0 | 100 | " |
| No. 9 | " | 0 | 100 | " |
| No. 10 | " | 0 | 100 | " |
| No. 11 | " | 0 | 100 | " |
| No. 12 | " | 0 | 100 | " |
| No. 13 | " | 0 | 100 | " |
| No. 14 | " | 0 | 100 | " |
| No. 15 | " | 0 | 100 | " |
| Reference Compound | | | | |
| No. 1 | 100 | 127.9 | 72.3 | None |
| No. 2 | " | 138.1 | 70.1 | " |
| No. 3 | " | 136.7 | 70.4 | " |
| No. 4 | " | 93.3 | 79.8 | " |
| No. 5 | " | 92.3 | 80.0 | " |
| No. 101 | " | 400.3 | 13.3 | " |
| No. 102 | " | 463.6 | 0 | " |
| No. 103 | " | 463.8 | 0 | " |
| No. 104 | " | 369.4 | 20.0 | " |
| No. 105 | " | 352.4 | 23.7 | " |
| No. 106 | " | 410.0 | 11.2 | " |
| No. 107 | " | 422.0 | 8.6 | " |
| No. 108 | " | 390.6 | 15.4 | " |
| No. 109 | " | 472.6 | 0 | " |
| No. 110 | " | 377.2 | 18.3 | " |
| No. 111 | " | 416.5 | 9.8 | " |
| No. 112 | " | 461.2 | 0 | " |
| No. 113 | " | 408.1 | 11.6 | " |
| No. 114 | " | 466.1 | 0 | " |
| Neo-Asozine Solution | 32.5 | 38.8 | 91.6 | " |
| Non-treated | — | 461.7 | 0 | " |

Neo-Asozine solution: ferric ammonium salt of methane arsonic acid, effective concentration 6.5%.

The reference compounds are ones disclosed in the German OLS No. 1,907,436 and British Pat. No. 1,217,868 and in the parent applications (No. 1–5).

Reference Compound
No. 1  3'-methyl-2-chlorobenzanilide
No. 2  3'-methoxy-2-chlorobenzanilide
No. 3  3'-methoxy-2-nitrobenzanilide
No. 4  3'-methoxy-2-acetyloxybenzanilide
No. 5  3'-methyl-2-methylbenzanilide
No. 101  2-chlorobenzanilide
No. 102  4'-methyl-2-chlorobenzanilide
No. 103  4'-methoxy-2-chlorobenzanilide
No. 104  2-bromobenzanilide
No. 105  2-iodobenzanilide
No. 106  2'-methyl-2-iodobenzanilide
No. 107  4'-methyl-2-iodobenzanilide
No. 108  2-nitrobenzanilide
No. 109  4'-methoxy-2-nitrobenzanilide
No. 110  2-methylbenzanilide
No. 111  2'-methyl-2-methylbenzanilide
No. 112  4'-methyl-2-methylbenzanilide
No. 113  2'-ethyl-2-methylbenzanilide
No. 114  4'-ethyl-2-methylbenzanilide

TEST EXAMPLE 2

Effect against on oat crown rust

Porcelain pots of a diameter of 9 cm were planted with each 20 seeds of oats, and the wettable powder preparation according to the composition No. 2 was diluted with water to a given concentration and sprayed in an amount of 20 ml per pot when the first leaf developed completely. The spores of oat crown rust (*Puccinia coronata Corda f. avenae Frikss*) collected from the lesions of diseased leaves were suspended in such a concentration as five spores would appear in the field of a microscope of a magnification of 150 times and sprayed in an amount of 1 ml per pot on the succeeding day of said spraying. After the inoculation the plants were maintained for 8 days in a high humidity chamber of 22° C. and 100% relative humidity and the number of lesions was counted. The controlling value was calculated from the number of lesions according to the following formula:

$$\text{Controlling value} = \frac{\text{Number of lesions in non-treated area} - \text{Number of lesions in treated area}}{\text{Number of lesions in non-treated area}} \times 100$$

Table 2

| Compound | Controlling Value | | |
|---|---|---|---|
| | 31.25 ppm | 125 ppm | 500 ppm |
| No. 2 | 95.4 | 100 | 100 |
| No. 4 | 96.2 | 100 | 100 |
| No. 5 | 95.6 | 100 | 100 |
| No. 6 | 97.2 | 100 | 100 |
| No. 7 | 98.5 | 100 | 100 |
| No. 8 | 95.1 | 100 | 100 |
| No. 10 | 97.4 | 100 | 100 |
| No. 11 | 90.7 | 100 | 100 |
| No. 13 | 93.9 | 100 | 100 |
| No. 15 | 92.1 | 100 | 100 |
| Plantvax* 50% wettable powder | 95.9 | 100 | 100 |

Plantvax: 5,6-dihydro-2-methyl-1,4-oxatine-3-carboxanilide-4,4-dioxide

TEST EXAMPLE 3

Effect on *cucumber Rhizoctonia solani*

Porcelain pots of a diameter of 12 cm were filled with infected soil prepared by diluting the *cucumber Rhizoctonia solani* cultivated in a bran medium 40 times with ordinary soil. 20 seeds of cucumber, previously coated with the wettable powder preparation of the Composition No. 2 in a concentration of the active ingredient of 0.05, 0.1 and 0.2% with respect to the weight of said seeds were planted in each pot. After the planting, the pots were maintained in a greenhouse, and the percentage of non-infected seedlings was determined when the plants reached the two-leaf stage.

$$\text{Normally grown seedling rate (\%)} = \frac{\text{Number of normally grown seedlings}}{\text{Number of total seedlings}} \times 100$$

Table 3

| Compound No. | Normally grown seedling rate % | | |
|---|---|---|---|
| | 0.05% | 0.1% | 0.2% |
| No. 2 | 80.0 | 89.2 | 100 |
| No. 3 | 97.7 | 100 | 100 |
| No. 5 | 98.7 | 100 | 100 |
| No. 7 | 97.0 | 100 | 100 |
| No. 10 | 95.2 | 100 | 100 |
| Compound No. 13 | 90.0 | 95.2 | 100 |
| Captan* 50% wettable powder | 8.9 | 24.9 | 66.1 |
| Non-treated | | 10.0 | |

Captan: N-(trichloromethyl-thio)-4-cyclohexene-1,2-dicarboximide

TEST EXAMPLE 4

Chemical injury on chrysanthemum leaf lesions

Porcelain pots of a diameter of 15 cm were planted with three seedlings each of chrysanthemum (Fuji), and the wettable powder preparation of the composition No. 2 diluted with water to a given concentration was sprayed in an amount of 50 ml per pot when the seedlings reached six-leaf stage. The pots were maintained in a greenhouse, and the frequency of the chemical injury was determined after 3 weeks.

Table 4

| Compound | Frequency of chemical injury | | |
|---|---|---|---|
| | 1000 ppm | 2000 ppm | 4000 ppm |
| No. 2 | — | — | — |
| No. 3 | — | — | — |
| No. 5 | — | — | — |
| No. 7 | — | — | — |
| No. 8 | — | — | — |
| No. 11 | — | — | — |
| No. 13 | — | — | — |
| No. 15 | — | — | — |
| Sicarol* 50% wettable powder | ++ | +++ | +++ |
| Plantvax* 50% wettable powder | +++ | +++ | +++ |

Note:
"—" indicates the absence of chemical injury while "+ - +++" indicate the presence of chemical injury in the increasing order.
*Sicarol: 2-methyl-5,6-dihydro-4H-pyran-3-carboxylic acid anilide
*Plantvax: 5,6-dihydro-2-methyl-1,4-oxatine-3-carboxanilide-4,4-dioxide

TEST EXAMPLE 5

Curing test of sheath blight of rice

The fungus of sheath blight cultured on potato culture medium (circular culture having a diameter of 9 mm) was inoculated on leaf sheaths of aquatic rices (kind: Kinnanpu) having five to six leaves planted in white porcelain pots having a diameter of 9 cm. On each pots 15 stains of aquatic rices were planted. After 2 days 50 ml of a wettable powder prepared according to Composition No. 2 and diluted with water to a predetermined concentration was sprayed on each pot and then the treated pots were placed in a greenhouse. After 8 days, the length of lesions of sheath blight formed or the leaf sheaths of aquatic rices were measured. Each test was carried out on three pots as one group.

$$\text{Protecting Value (\%)} = \left(1 - \frac{\text{Total length of lesions in treated area}}{\text{Total length of lesions in untreated area}}\right) \times 100$$

Table 5

| Test Compound | Concentration (ppm) | Total length of lesion (mm) | Protective Value | Toxicity |
|---|---|---|---|---|
| Compound | | | | |
| No. 1 | 500 | 28.2 | 91.6 | None |
| No. 2 | " | 0 | 100 | " |
| No. 3 | " | 40.5 | 87.9 | " |
| No. 4 | " | 35.6 | 89.4 | " |
| No. 5 | " | 0 | 100 | " |
| No. 6 | " | 21.2 | 93.7 | " |
| No. 7 | " | 18.6 | 94.5 | " |
| No. 8 | " | 26.5 | 92.1 | " |
| No. 9 | " | 0 | 100 | " |
| No. 10 | " | 32.4 | 90.4 | " |
| No. 11 | " | 0 | 100 | " |
| No. 12 | " | 11.1 | 96.7 | " |
| No. 13 | " | 0 | 100 | " |
| No. 14 | " | 10.9 | 96.8 | " |
| No. 15 | " | 22.2 | 93.4 | " |
| Reference Compound | | | | |
| No. 101 | " | 141.2 | 58.0 | " |
| No. 102 | " | 135.6 | 59.6 | " |
| No. 103 | " | 161.8 | 51.8 | " |
| No. 104 | " | 156.2 | 53.5 | " |
| No. 105 | " | 148.6 | 55.8 | " |
| No. 106 | " | 201.2 | 40.1 | " |
| No. 107 | " | 212.4 | 36.8 | " |
| No. 108 | " | 198.6 | 40.9 | " |

Table 5-continued

| Test Compound | Concentration (ppm) | Total length of lesion (mm) | Protective Value | Toxicity |
|---|---|---|---|---|
| No. 109 | " | 168.4 | 50.0 | " |
| No. 110 | " | 186.2 | 44.6 | " |
| No. 111 | " | 192.1 | 42.8 | " |
| No. 112 | " | 200.4 | 40.4 | " |
| No. 113 | " | 138.6 | 58.8 | " |
| No. 114 | " | 171.9 | 48.8 | " |
| No. 1 | " | 202.5 | 39.7 | " |
| No. 2 | " | 197.8 | 41.1 | " |
| No. 3 | " | 169.6 | 49.5 | " |
| No. 4 | " | 188.2 | 44.0 | " |
| No. 5 | " | 176.6 | 47.4 | " |
| Untreated Area | — | 336.0 | 0 | " |

Reference Compounds 1 - 5 and 101 - 114 are the same as in Test Example 1.

We claim:

1. A benzanilide derivative having the following general formula (I):

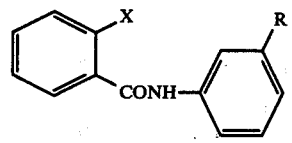

wherein X stands for a halogen atom or a methyl radical; and R stands for an alkyl or alkoxy radical containing 3 to 6 carbon atoms provided that R represents an alkyl radical containing 3 to 6 carbon atoms when X is a methyl radical.

2. A benzanilide derivative according to claim 1 represented by the following general formula (I''):

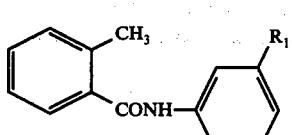

wherein $R_1$ stands for an alkyl radical containing 3 to 6 carbon atoms.

3. 3'-isopropyl-2-methylbenzanilide.
4. 3'-tert-butyl-2-methylbenzanilide.
5. 3'-iso-propyl-2-iodobenzanilide.
6. 3'-n-propoxy-2-iodobenzanilide.
7. 3'-isopropoxy-2-iodobenzanilide.
8. 3'-n-butyloxy-2-iodobenzanilide.
9. 3'-iso-butyloxy-2-iodobenzanilide.
10. 3'-sec-butyloxy-2-iodobenzanilide.
11. An agricultural and horticultural composition containing as the active ingredient a fungicidally or germicidally effective amount of a benzanilide derivative represented by the general formula (I):

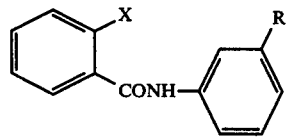

wherein X stands for a halogen atom, or methyl radical; and R stands for an alkyl or alkoxy radical containing 3 to 6 carbon atoms provided that R represents an alkyl radical containing 3 to 6 carbon atoms when X is a methyl radical and a carrier.

12. An agricultural and horticultural germicide according to claim 11 wherein the benzanilide derivative is represented by the general formula (I'):

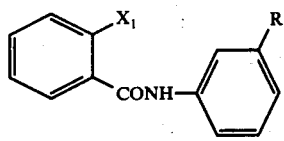

wherein $X_1$ is a halogen atom, and R is an alkyl or alkoxy radical containing 3 to 6 carbon atoms.

13. An agricultural and horticultural germicide according to claim 11 wherein the the benzanilide derivative is represented by the general formula (I''):

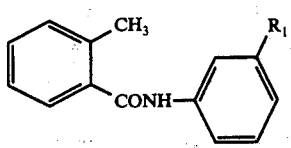

wherein $R_1$ is an alkyl radical containing 3 to 6 carbon atoms.

14. A method for killing fungi and germs on plants which comprises applying to plants or soil a fungicidally or germicidally effective amount of a benzanilide derivative represented by the general formula (I):

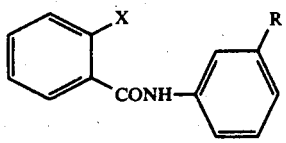

wherein X stands for a halogen atom or methyl radical; and R stands for an alkyl or alkoxy radical containing 3 to 6 carbon atoms provided that R represents an alkyl radical with 3 to 6 carbon atoms when X is a methyl radical.

15. A method according to claim 14 wherein the benzanilide derivative has the general formula (I'):

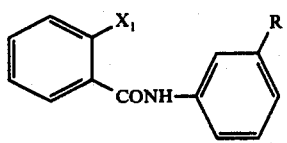

wherein $X_1$ is a halogen atom, and R is an alkyl or alkoxy radical with 3 to 6 carbon atoms.

16. A method according to claim 14 wherein the benzanilide derivative has the general formula (I''):

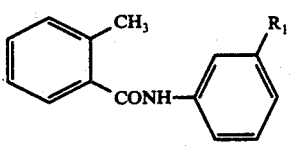

wherein $R_1$ is an alkyl radical with 3 to 6 carbon atoms.

* * * * *